(12) United States Patent
Tang et al.

(10) Patent No.: US 7,384,921 B2
(45) Date of Patent: *Jun. 10, 2008

(54) POLYMORPHIC FORMS OF 6-11 BICYCLIC KETOLIDE DERIVATIVES

(75) Inventors: Datong Tang, Watertown, MA (US); Guoyou Xu, Newton, MA (US); Yonghua Gai, North Grafton, MA (US); Zhe Wang, Hockessin, DE (US); Yat Sun Or, Watertown, MA (US); Hui-Yin Li, Hockessin, DE (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 95 days.

This patent is subject to a terminal disclaimer.

(21) Appl. No.: 11/057,476

(22) Filed: Feb. 14, 2005

(65) Prior Publication Data

US 2005/0203035 A1 Sep. 15, 2005

Related U.S. Application Data

(60) Provisional application No. 60/615,803, filed on Oct. 4, 2004, provisional application No. 60/546,433, filed on Feb. 20, 2004.

(51) Int. Cl.
*A61K 31/70* (2006.01)
*C07H 17/08* (2006.01)

(52) U.S. Cl. .................................. 514/29; 536/7.4
(58) Field of Classification Search .................. 536/7.4; 514/29
See application file for complete search history.

(56) References Cited

U.S. PATENT DOCUMENTS

| | | | |
|---|---|---|---|
| 5,118,799 A * | 6/1992 | Rossignol | ........... 536/7.2 |
| 5,780,605 A | 7/1998 | Or et al. | |
| 5,922,683 A | 7/1999 | Or et al. | |
| 6,046,171 A | 4/2000 | Or et al. | |
| 6,054,435 A | 4/2000 | Or et al. | |
| 6,075,133 A | 6/2000 | Or et al. | |
| 6,245,903 B1 | 6/2001 | Karimian et al. | |
| 6,274,715 B1 | 8/2001 | Or et al. | |
| 6,355,620 B1 | 3/2002 | Ma et al. | |
| 6,764,998 B1 | 7/2004 | Wang et al. | |
| 6,878,691 B2 | 4/2005 | Or et al. | |
| 2003/0082107 A1 | 5/2003 | Dugger, III | |
| 2004/0053861 A1 | 3/2004 | Or et al. | |
| 2004/0121966 A1 | 6/2004 | Li et al. | |
| 2004/0142029 A1 | 7/2004 | Becourt et al. | |
| 2004/0157787 A1 | 8/2004 | Or et al. | |
| 2004/0171818 A1 | 9/2004 | Xu et al. | |
| 2004/0266998 A1 | 12/2004 | Or et al. | |
| 2005/0009761 A1 | 1/2005 | Or et al. | |
| 2005/0009763 A1 | 1/2005 | Or et al. | |
| 2005/0014707 A1 | 1/2005 | Wang et al. | |
| 2005/0159370 A1 | 7/2005 | Or et al. | |
| 2005/0171033 A1 | 8/2005 | Qiu et al. | |

FOREIGN PATENT DOCUMENTS

| | | |
|---|---|---|
| WO | WO 99/21864 | 5/1999 |
| WO | WO 02/42315 A2 | 5/2002 |
| WO | WO 03/074029 A1 | 9/2003 |
| WO | WO 03/095466 A1 | 11/2003 |
| WO | WO 03/097659 A1 | 11/2003 |
| WO | WO 2004/035063 A1 | 4/2004 |
| WO | WO 2004/056344 A1 | 7/2004 |

OTHER PUBLICATIONS

Rouhi, "Right Stuff", Chemical and Enginnering News, Feb. 24, 2003, pp. 32-35.*
U.S. Appl. No. 11/257,680, filed Oct. 25, 2005, Wang et al.
U.S. Appl. No. 11/154,260, filed Jun. 16, 2005, Deqiang Niu et al.
U.S. Appl. No. 11/029,640, filed Jan. 5, 2005, Nha Huu Vo et al.
U.S. Appl. No. 11/122,251, filed May 4, 2005, Guoqiang Wang et al.
8th International Antibacterial Drug Discovery and Development Summit, *Strategic Research Institute*, Mar. 24-25, 2003, Princeton, NJ.

* cited by examiner

*Primary Examiner*—Elli Peselev
(74) *Attorney, Agent, or Firm*—Carolyn S. Elmore; Elmore Patent Law Group

(57) ABSTRACT

The present invention includes EP-13420 polymorphic crystalline forms: Form I, Form II, Form Ia, and monohydrate and amorphous EP-13420 which posses distinct physical properties. In another embodiment of the present invention, there are provided methods of producing the various polymorphic forms in pure form or in combination with one another. The present invention also provides pharmaceutical compositions and formulations comprising the polymorphic and amorphous forms and methods of treating bacterial infections by administering the pharmaceutical compositions to a subject in need of such treatment.

10 Claims, 15 Drawing Sheets

POLYMORPHIC FORMS OF 6-11 BICYCLIC KETOLIDE DERIVATIVES

RELATED APPLICATIONS

This application claims the benefit of U.S. Provisional Application No. 60/546,433, filed on Feb. 20, 2004, and U.S. Provisional Application No. 60/615,803, filed on Oct. 4, 2004. The entire contents of both provisional applications are hereby incorporated by reference.

TECHNICAL FIELD

The present invention relates to polymorphic forms of a 6-11 bicyclic ketolide derivative known as EP-13420.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) shows a wide range of characteristics (antibacterial spectrum, side-effects and bioavailability). Among the commonly used macrolides are erythromycin, clarithromycin, and azithromycin. Macrolides possessing a 3-oxo moiety in place of the 3-cladinose sugar are known as ketolides and have shown enhanced activity towards gram-negative bacteria and macrolide resistant gram-positive bacteria. The search for macrolide compounds which are active against $MLS_B$-resistant strains ($MLS_B$=Macrolides-Lincosamides-type B Streptogramines) has become a major goal, together with retaining the overall profile of the macrolides in terms of stability, tolerance and pharmacokinetics.

Polymorphic forms of a given drug substance or API, as administered by itself or formulated as a drug product (also known as the final or finished dosage form), are well known in the pharmaceutical arts to affect, for example, the solubility, stability, flowability, fractability, and compressibility of drug substances and the safety and efficacy of drug products. (see, e.g., Knapman, K. *Modern Drug Discoveries* 53 (March 2000)). So critical are the potential effects of different polymorphic forms in a single drug substance on the safety and efficacy of the respective drug product(s) that the United States Food and Drug Administration (FDA) requires each drug substance manufacturer, at least, to control its synthetic processes such that the percentages of the various respective polymorphic forms, when present, must be controlled and consistent among batches and within the drug substance/product's specification as approved by the FDA.

SUMMARY OF THE INVENTION

The present invention relates to polymorphic forms of EP-13420 which has the following formula:

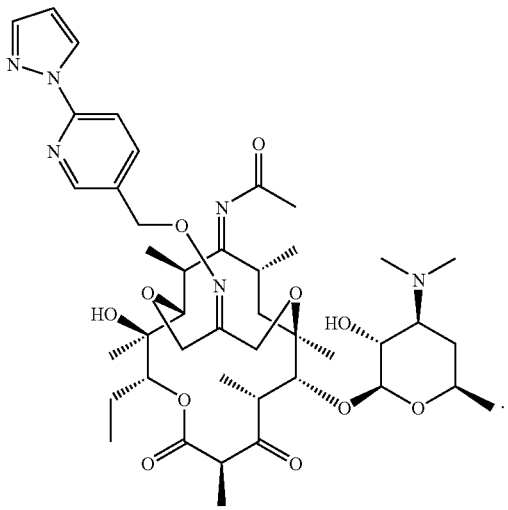

(EP-13420)

The present invention includes polymorphic crystalline forms: Form I, Form II, Form Ia, and amorphous and monohydrate EP-13420 which posses distinct physical properties. In another embodiment of the present invention, there are provided methods of producing the various polymorphic forms in pure form or in combination with one another. Other salts and polymorphs produced according to the methods of the invention include EP 13420 malate, HBr, L-tartarate, ethane-1,2-disulfonate, DL mandelate, orotate, S-mandelate, salicylate, gentisate, benzenesulfonate, maleate, toluene sulfonate, sulfate, HCl, malonate, and methanesulfonate. The present invention also provides pharmaceutical compositions and pharmaceutical formulations comprising the polymorphic, amorphous, or monohydrate forms of EP-13420. Pharmaceutical formulations of the invention include tablets, capsules, solutions, sachets or powder for suspension dosage forms comprising a polymorphic form or other form of EP13420 and one or more pharmaceutically acceptable excipients, for use in the treatment of bacterial and protozoan infections and inflammatory conditions.

DETAILED DESCRIPTION OF THE INVENTION

The present invention is directed to Form I, II, Ia, and monhydrate EP-13420 as well as amorphous EP-13420, and processes for the preparation thereof, and methods of treating bacterial infections in a subject in need of such treatment using said polymorphic and amorphous forms of EP-13420 or pharmaceutical compositions thereof. The polymorphic and amorphous forms of the present invention were characterized using differential scanning calorimetry (DSC) and X-ray powder diffraction (XRD) analysis as discussed below. Characterization with either of these techniques reveals distinctive peaks for each particular polymorphic form, whether in a pure state or not. For example, pure Form I, provides a distinct range of peaks when analyzed by XRD. These significant peaks will be present with XRD analysis for pure Form I as well as for samples containing Form I in combination with other polymorphic forms of EP-13420.

Figure 1:
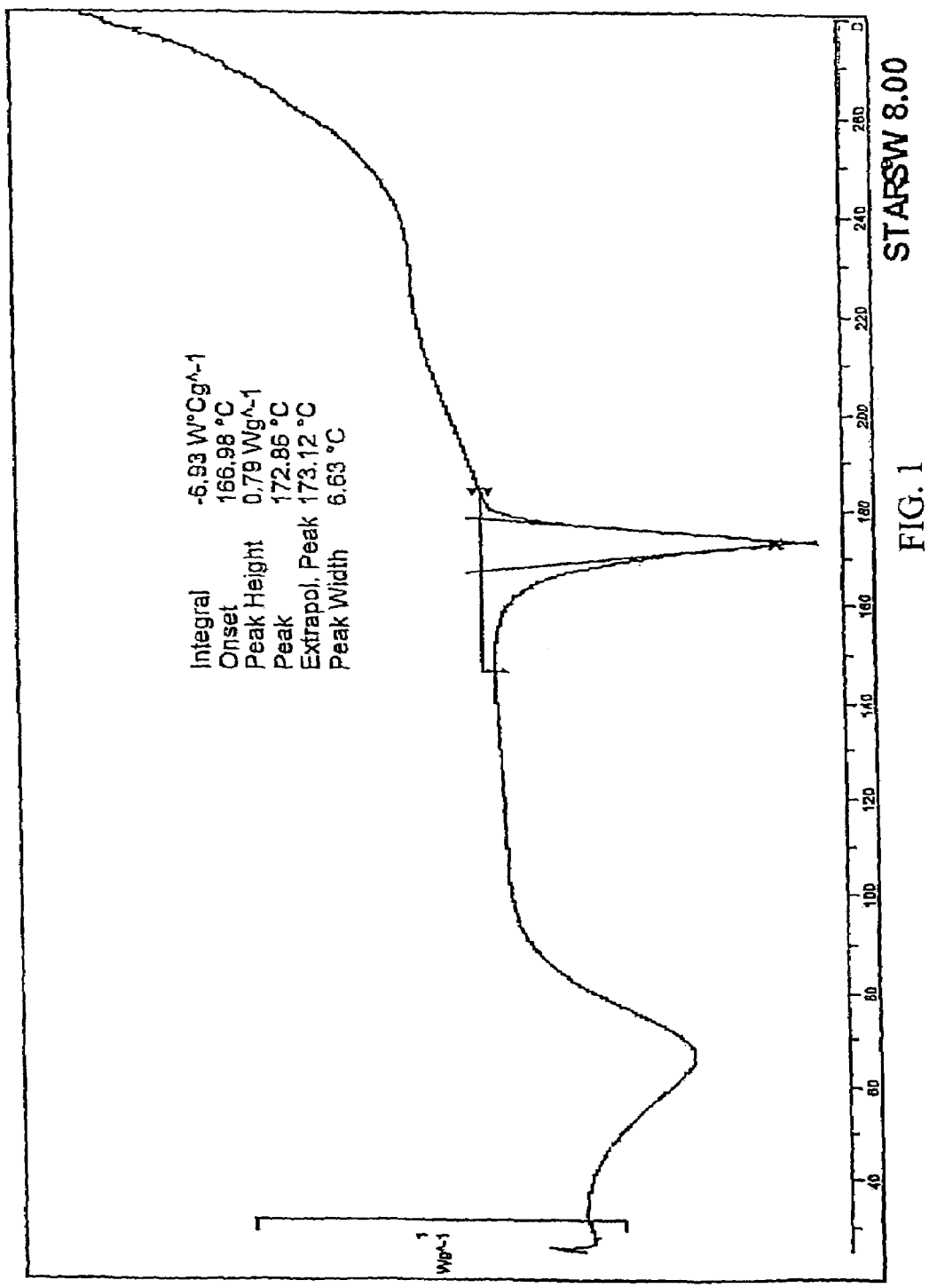
FIG. 1 illustrates a Differential Scanning Calorimetry (DSC) thermogram for Form I of EP-13420.
Figure 2:
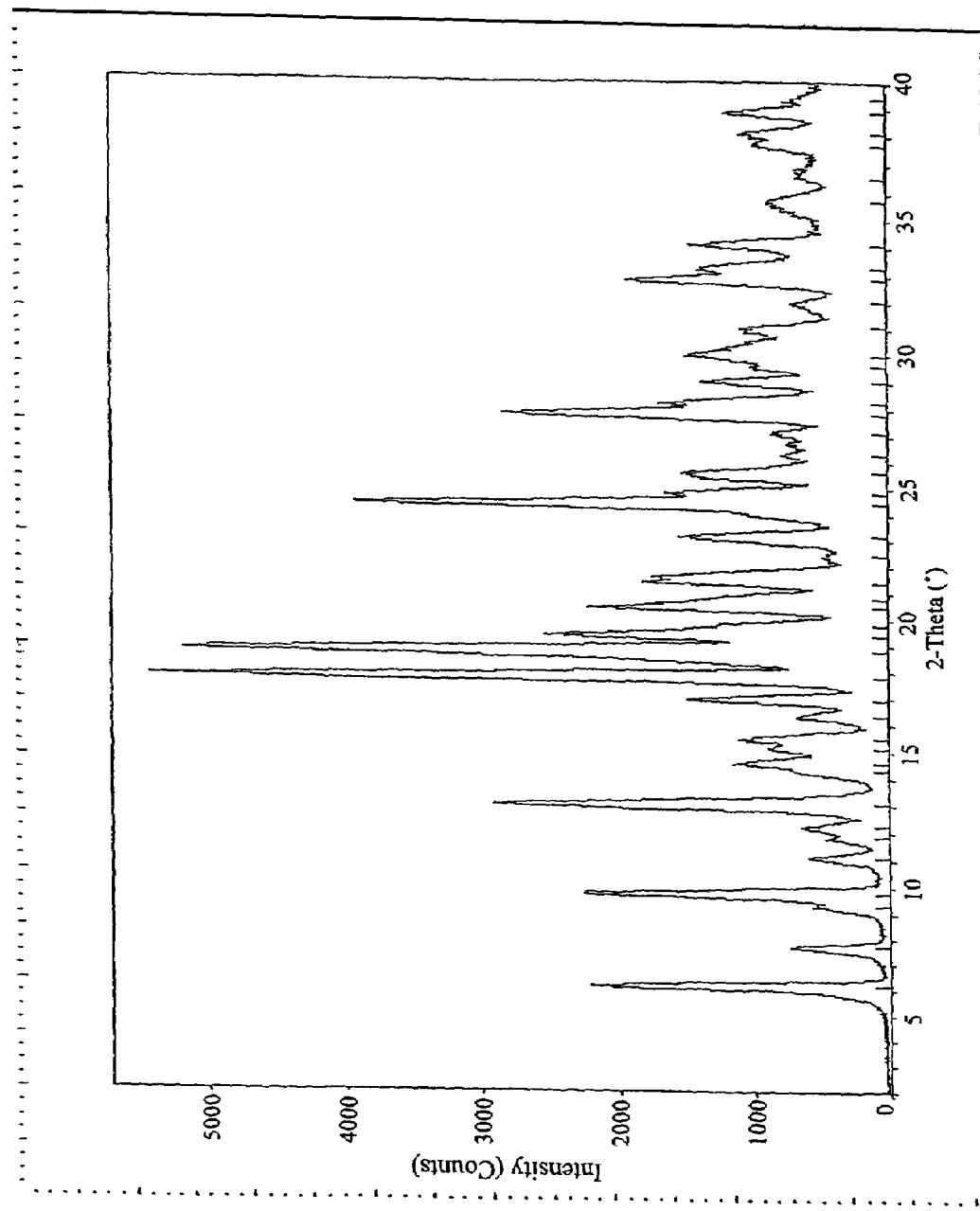
FIG. 2 illustrates an X-ray powder diffraction (XRD) pattern for Form I EP-13420.
Figure 3:
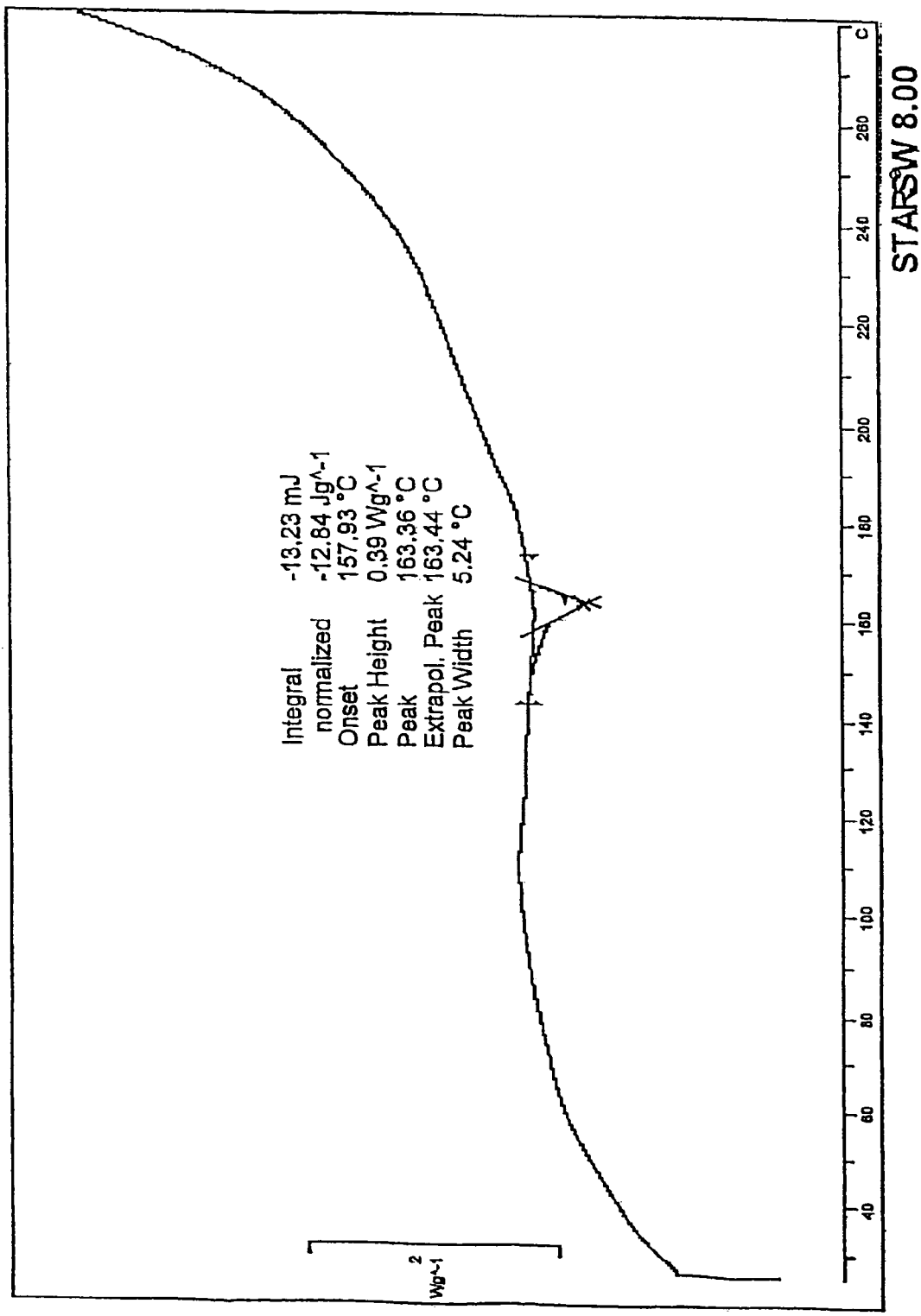
FIG. 3 illustrates a DSC thermogram of Form II EP-13420.
Figure 4:
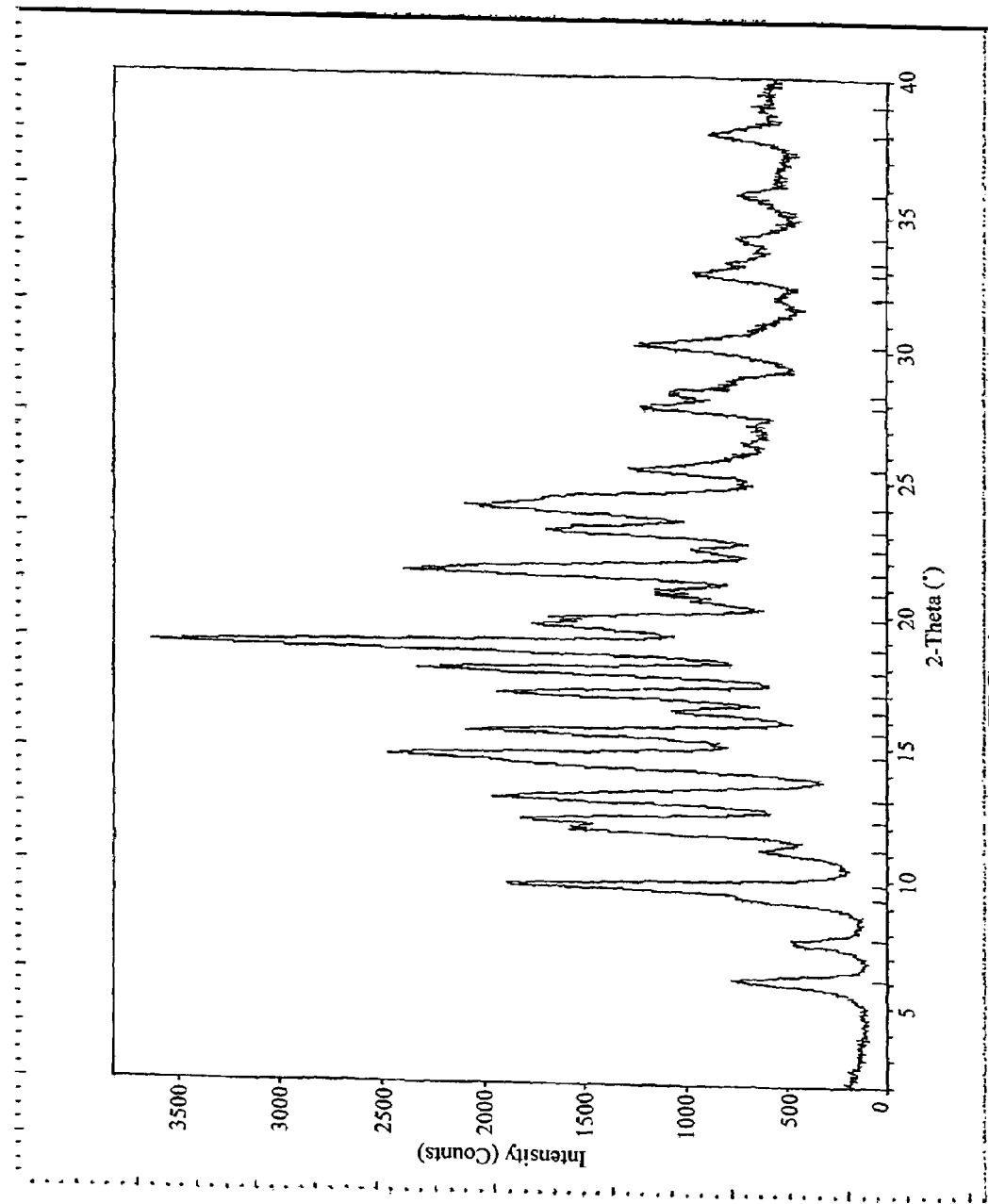
FIG. 4 illustrates an XRD pattern for Form II EP-13420.
Figure 5:
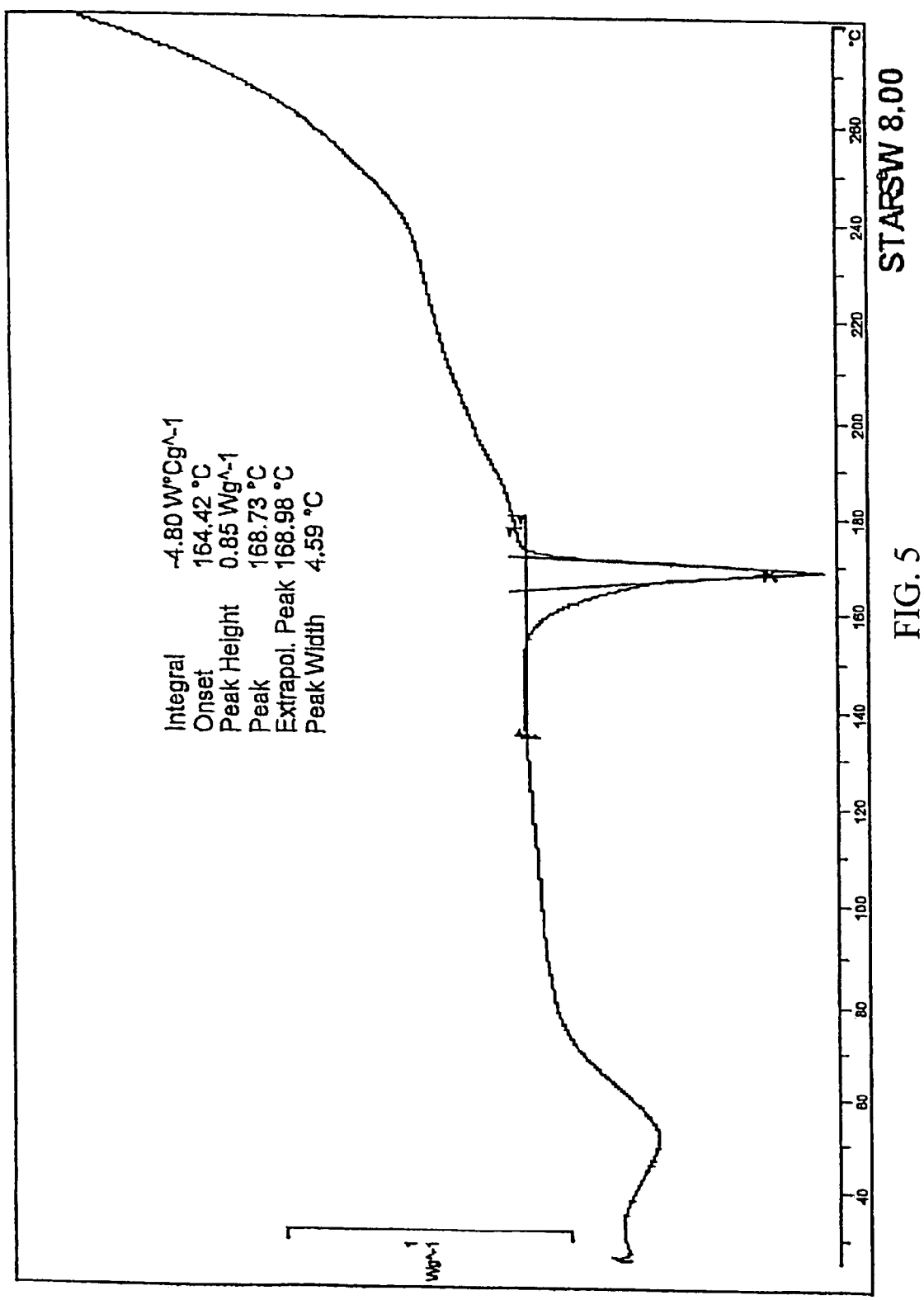
FIG. 5 illustrates a DSC thermogram for Form Ia EP-13420.
Figure 6:
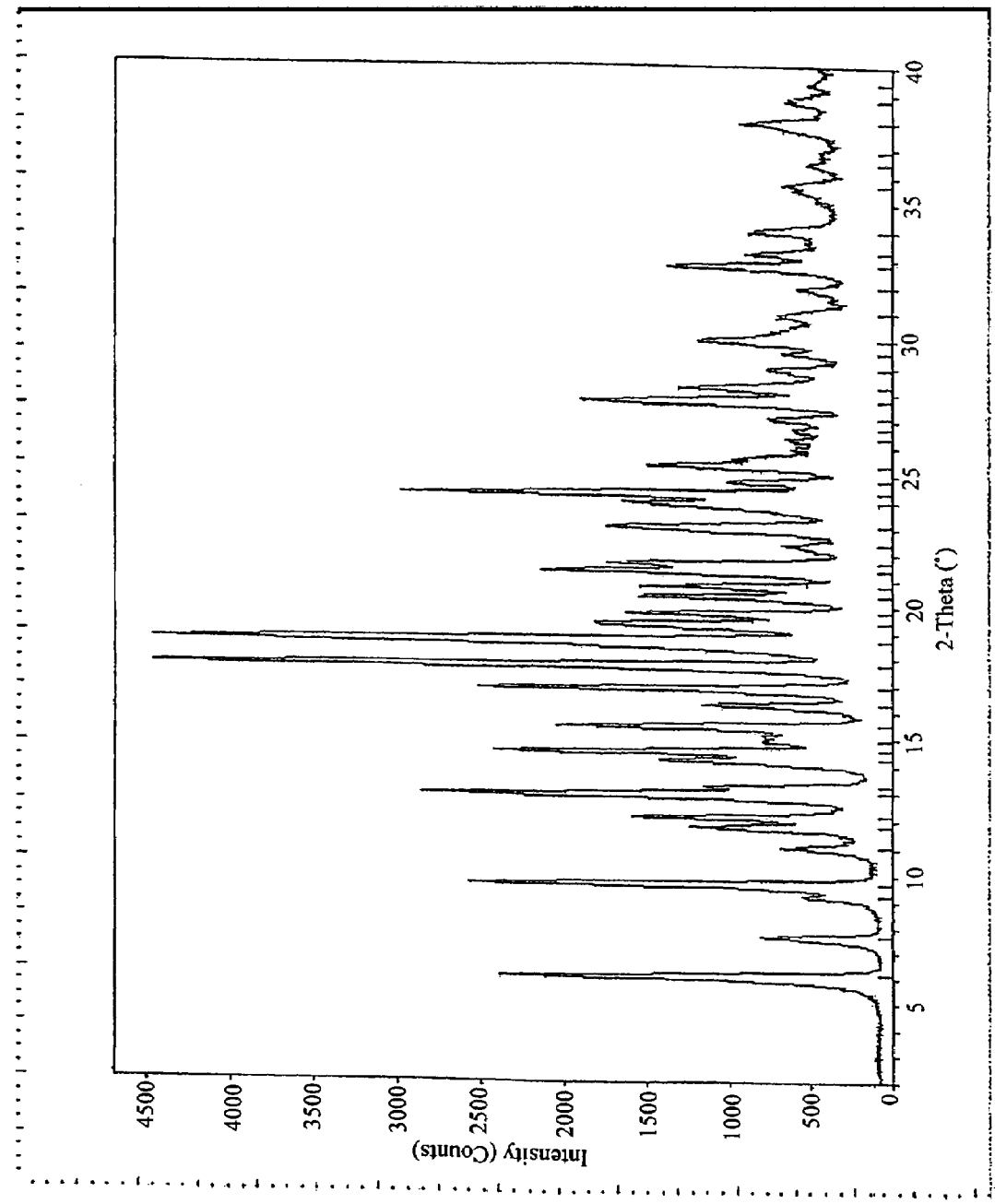
FIG. 6 illustrates an XRD pattern for Form Ia EP-13420.
Figure 7:
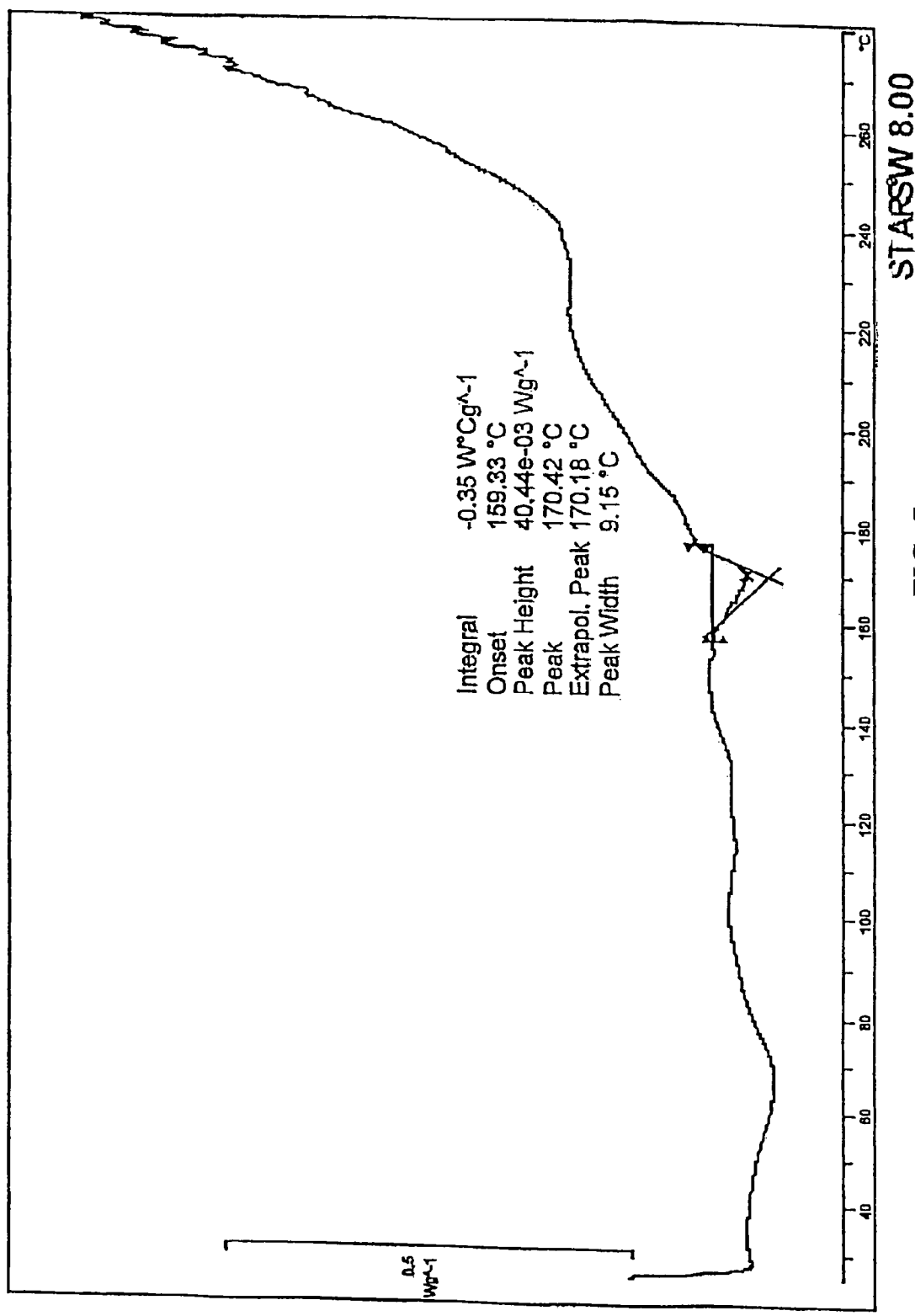
FIG. 7 illustrates a DSC thermogram for amorphous EP-13420.
Figure 8:
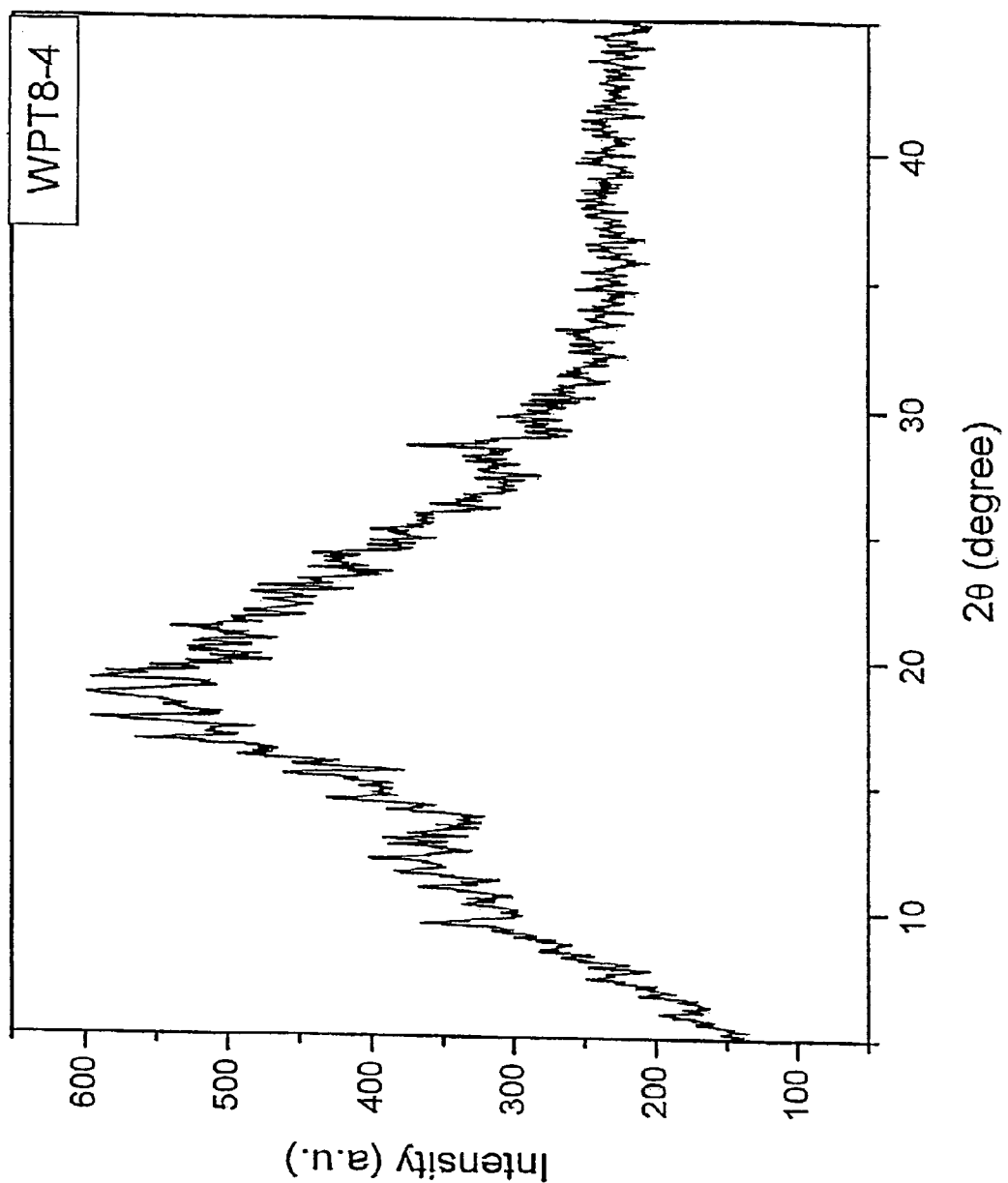
FIG. 8 illustrates an XRD pattern for amorphous EP-13420.

FIG. 1 presents a DSC thermogram for Form I EP-13420 which provides an endothermic peak of about 173° C. (onset at about 167° C.). FIG. 2 presents an XRD pattern for Form I EP-13420, significant peak values of which are provided in Table 1 below. FIG. 3 presents a DSC thermogram for Form II EP-13420 which provides an endothermic peak at about 163° C. (onset of about 158° C.). FIG. 4 presents an XRD pattern for Form II EP-13420, significant peak values of which are provided in Table 2 below. FIG. 5 presents a DSC thermogram for Form Ia EP-13420 which provides an endothermic peak at about 169° C. (onset of about 164° C.). FIG. 6 presents an XRD pattern for Form Ia EP-13420, significant peak values of which are provided in Table 3 below. FIG. 7 presents a DSC thermogram for amorphous EP-13420 which provides an endothermic peak at about 170° C. (onset of about 159° C.). FIG. 8 presents an XRD pattern for amorphous EP-13420. It is well known by one of ordinary skill in the art that lot-to-lot variations of crystal shape and/or size, as well as variations among instruments and calibration of such instruments, can appear as a preferred orientation in the X-ray diffraction patterns. Said preferred pattern can be seen as variations in an amount of up to about 20%.

TABLE 1

X-Ray Powder Diffraction of Form I EP-13420

| 2-Theta (degrees) | d (Å) | Strength[1] | I % (Area) |
|---|---|---|---|
| 6.1 | 14.38 | s | 42.2 |
| 7.7 | 11.47 | m | 12.8 |
| 9.3 | 9.51 | m | 11.3 |
| 9.8 | 9.01 | m | 50.4 |
| 11.1 | 7.95 | m | 10.1 |
| 11.8 | 7.47 | w | 4.2 |
| 12.2 | 7.23 | m | 9.0 |
| 13.0 | 6.78 | vs | 61.1 |
| 14.3 | 6.19 | m | 15.6 |
| 14.5 | 6.07 | s | 32.1 |
| 15.1 | 5.85 | s | 35.3 |
| 15.5 | 5.72 | s | 30.2 |
| 16.3 | 5.42 | w | 7.7 |
| 16.9 | 5.23 | s | 20.9 |
| 17.8 | 4.97 | vs | 100.0 |
| 18.8 | 4.72 | vs | 83.7 |
| 19.4 | 4.56 | vs | 50.2 |

TABLE 1-continued

X-Ray Powder Diffraction of Form I EP-13420

| 2-Theta (degrees) | d (Å) | Strength[1] | I % (Area) |
|---|---|---|---|
| 19.8 | 4.48 | s | 22.9 |
| 20.5 | 4.33 | s | 37.3 |
| 20.8 | 4.27 | s | 26.0 |
| 21.4 | 4.14 | s | 35.0 |
| 22.5 | 3.96 | vw | 0.4 |
| 23.2 | 3.83 | s | 23.8 |
| 24.4 | 3.64 | s | 85.9 |
| 24.9 | 3.58 | s | 40.5 |
| 25.6 | 3.47 | m | 19.9 |
| 26.3 | 3.38 | vw | 0.9 |
| 27.1 | 3.28 | w | 4.6 |
| 27.9 | 3.20 | vs | 65.2 |
| 28.3 | 3.15 | s | 41.3 |
| 29.0 | 3.07 | m | 10.1 |
| 29.6 | 3.01 | w | 6.0 |
| 30.0 | 2.98 | s | 21.8 |
| 31.0 | 2.88 | w | 5.8 |
| 32.0 | 2.79 | w | 3.6 |
| 32.8 | 2.72 | s | 41.9 |
| 33.2 | 2.69 | s | 32.2 |
| 34.1 | 2.63 | m | 13.9 |
| 35.7 | 2.52 | m | 14.6 |
| 36.5 | 2.46 | w | 3.5 |
| 37.7 | 2.38 | m | 14.5 |
| 38.1 | 2.36 | m | 17.2 |
| 38.9 | 2.31 | m | 14.2 |
| 39.4 | 2.28 | w | 4.7 |
| 40.4 | 2.23 | m | 9.2 |
| 42.0 | 2.15 | vw | 1.1 |
| 42.7 | 2.12 | w | 7.4 |
| 43.4 | 2.08 | w | 4.3 |
| 44.8 | 2.02 | w | 5.9 |
| 45.7 | 1.98 | w | 4.4 |
| 46.9 | 1.94 | w | 3.6 |
| 47.5 | 1.91 | w | 3.9 |
| 48.1 | 1.89 | w | 4.8 |
| 48.8 | 1.86 | vw | 1.3 |
| 49.8 | 1.83 | vw | 1.8 |
| 50.8 | 1.80 | w | 6.0 |
| 52.2 | 1.75 | vw | 0.8 |
| 53.3 | 1.72 | w | 4.5 |
| 54.6 | 1.68 | w | 2.0 |
| 57.9 | 1.59 | vw | 0.8 |

TABLE 2

X-Ray Powder Diffraction of Form II EP-13420

| 2-Theta (degrees) | d (Å) | Strength[1] | I % (Area) |
|---|---|---|---|
| 6.1 | 14.45 | s | 25.7 |
| 7.8 | 11.39 | m | 11.7 |
| 9.3 | 9.48 | s | 34.0 |
| 9.8 | 8.99 | vs | 63.1 |
| 11.2 | 7.93 | m | 14.8 |
| 12.2 | 7.25 | vs | 56.5 |
| 13.0 | 6.80 | vs | 51.4 |
| 14.6 | 6.05 | vs | 100.0 |
| 15.5 | 5.70 | s | 36.6 |
| 16.3 | 5.42 | m | 12.3 |
| 17.0 | 5.22 | s | 37.0 |
| 17.8 | 4.97 | s | 37.7 |
| 18.7 | 4.73 | vs | 77.0 |
| 19.9 | 4.47 | s | 31.7 |
| 20.8 | 4.26 | m | 10.5 |
| 21.6 | 4.12 | vs | 54.9 |
| 22.5 | 3.95 | w | 3.1 |
| 23.1 | 3.84 | m | 19.6 |
| 24.0 | 3.70 | vs | 57.0 |
| 25.5 | 3.50 | m | 18.9 |
| 27.9 | 3.20 | s | 20.1 |
| 28.3 | 3.15 | s | 40.1 |

TABLE 2-continued

X-Ray Powder Diffraction of Form II EP-13420

| 2-Theta (degrees) | d (Å) | Strength[1] | I % (Area) |
|---|---|---|---|
| 30.1 | 2.96 | s | 29.7 |
| 32.0 | 2.79 | vw | 1.5 |
| 32.8 | 2.73 | m | 17.5 |
| 33.3 | 2.69 | m | 12.8 |
| 34.2 | 2.62 | w | 4.9 |
| 35.8 | 2.51 | w | 7.7 |
| 38.0 | 2.37 | m | 10.9 |
| 39.0 | 2.31 | vw | 1.4 |
| 40.5 | 2.23 | w | 5.2 |
| 42.5 | 2.13 | w | 2.9 |
| 43.6 | 2.08 | w | 4.6 |
| 45.6 | 1.99 | w | 4.5 |
| 47.0 | 1.93 | w | 3.3 |
| 50.7 | 1.80 | w | 2.7 |

TABLE 3

X-Ray Powder Diffraction of Form Ia EP-13420

| 2-Theta (degrees) | d (Å) | Strength[1] | I % (Area) |
|---|---|---|---|
| 6.1 | 14.39 | vs | 54.4 |
| 7.7 | 11.52 | m | 16.6 |
| 9.3 | 9.54 | m | 18.2 |
| 9.7 | 9.10 | vs | 55.3 |
| 11.1 | 7.99 | m | 13.9 |
| 11.8 | 7.49 | s | 22.0 |
| 12.2 | 7.27 | s | 24.9 |
| 13.0 | 6.81 | vs | 65.8 |
| 13.2 | 6.68 | s | 35.3 |
| 14.2 | 6.23 | s | 31.4 |
| 14.6 | 6.08 | vs | 51.3 |
| 14.9 | 5.93 | s | 45.6 |
| 15.5 | 5.72 | vs | 54.6 |
| 16.3 | 5.44 | m | 18.2 |
| 16.9 | 5.24 | s | 42.7 |
| 17.8 | 4.99 | vs | 74.8 |
| 18.7 | 4.73 | vs | 100.0 |
| 19.4 | 4.57 | s | 47.9 |
| 19.8 | 4.48 | s | 25.0 |
| 20.4 | 4.34 | s | 21.7 |
| 20.8 | 4.26 | m | 18.1 |
| 21.4 | 4.15 | vs | 50.9 |
| 21.7 | 4.09 | s | 46.9 |
| 22.4 | 3.96 | w | 5.1 |
| 23.1 | 3.85 | s | 33.1 |
| 24.0 | 3.70 | vs | 58.3 |
| 24.4 | 3.65 | vs | 54.7 |
| 24.8 | 3.59 | w | 5.4 |
| 25.4 | 3.51 | s | 28.2 |
| 26.3 | 3.38 | vw | 1.6 |
| 26.7 | 3.33 | vw | 1.8 |
| 27.1 | 3.29 | w | 5.1 |
| 27.8 | 3.21 | s | 35.9 |
| 28.3 | 3.16 | s | 30.9 |
| 29.0 | 3.08 | w | 5.7 |
| 29.6 | 3.02 | vw | 1.7 |
| 30.0 | 2.97 | s | 26.3 |
| 31.0 | 2.88 | w | 5.3 |
| 32.0 | 2.80 | w | 5.6 |
| 32.8 | 2.73 | s | 23.4 |
| 33.2 | 2.69 | m | 9.4 |
| 34.0 | 2.64 | m | 8.9 |
| 35.7 | 2.51 | m | 11.8 |
| 36.5 | 2.46 | w | 4.5 |
| 36.9 | 2.43 | w | 2.5 |
| 38.0 | 2.37 | m | 16.5 |
| 38.8 | 2.32 | w | 4.6 |
| 39.4 | 2.28 | vw | 1.0 |
| 40.2 | 2.24 | w | 5.1 |
| 40.6 | 2.22 | m | 8.7 |
| 41.0 | 2.20 | w | 2.1 |
| 41.2 | 2.15 | w | 2.2 |
| 42.5 | 2.12 | w | 4.2 |
| 43.6 | 2.08 | w | 7.2 |
| 44.7 | 2.03 | w | 3.6 |
| 45.7 | 1.98 | m | 8.1 |
| 46.9 | 1.93 | w | 5.8 |
| 47.3 | 1.92 | w | 5.7 |
| 48.1 | 1.89 | w | 2.3 |
| 48.7 | 1.87 | vw | 0.5 |
| 50.7 | 1.80 | w | 3.7 |
| 51.3 | 1.78 | w | 2.9 |
| 57.9 | 1.59 | vw | 1.2 |

[1]vs = very strong (I > 50%); s = strong (I > 20%); m = moderate (20% > I > 8%); w = weak (8% > I > 4%); vw = very weak (I < 4%).

The XRD peaks shown in Table 1 demonstrated that the significant peaks of Form I (greater than 8%) are typically located at 2-Theta (2θ) angles of about 6.1, 7.7, 9.3, 9.8, 11.1, 12.2, 13.0, 14.3, 14.5, 15.1, 15.5, 16.9, 17.8, 18.8, 19.4, 19.8, 20.5, 20.8, 21.4, 23.2, 24.4, 24.9, 25.6, 27.9, 28.3, 29.0, 30.0, 32.8, 33.2, 34.1, 35.7, 37.7, 38.1, 38.9, and 40.4°. For Form II, the significant XRD peaks (greater than 8%), as demonstrated in Table 2, are typically located at 2-Theta (2θ) angles of about 6.1, 9.3, 9.8, 11.2, 12.2, 13.0, 14.6, 15.5, 16.3, 17.0, 17.8, 18.7, 19.9, 20.8, 21.6, 23.1, 24.0, 25.5, 27.9, 28.3, 30.1, 32.8, 33.3, and 38.0°. For Form Ia, the significant XRD peaks (greater than 8%), as demonstrated in Table 3, are typically located at 2-Theta (2θ) angles of about 6.1, 7.7, 9.3, 9.7, 11.1, 11.8, 12.2, 13.0, 13.2, 14.2, 14.6, 14.9, 15.5, 16.3, 16.9, 17.8, 18.7, 19.4, 19.8, 20.4, 20.8, 21.4, 21.7, 23.1, 24.0, 24.4, 25.4, 27.8, 28.3, 30.0, 32.8, 33.2, 34.0, 35.7, 38.0, 40.6, and 44.7°.

More preferably, the polymorphic forms of the present invention can be characterized by the 2-Theta (2θ) angles corresponding to strong XRD pattern peaks (I >20%) of each form. The strong XRD pattern peaks which are characteristic of Form I are typically located at 2-Theta (2θ) angles of about 6.1, 13.0, 14.3, 14.5, 15.1, 15.5, 16.9, 17.8, 18.8, 19.4, 19.8, 20.5, 20.8, 21.4, 23.2, 24.4, 24.9, 27.9, 28.3, 30.0, 32.8, and 33.2°. The strong XRD pattern peaks which are characteristic of Form II are typically located at 2-Theta (2θ) angles of about 6.1, 9.3, 9.8, 12.2, 13.0, 14.6, 15.5, 17.0, 17.8, 18.7, 19.9, 21.6, 24.0, 27.9, 28.3, and 30.1°. The strong XRD pattern peaks which are characteristic of Form Ia are typically located at 2-Theta (2θ) angles of about 6.1, 9.7, 11.8, 12.2, 13.0, 13.2, 14.2, 14.6, 14.9, 15.5, 16.9, 17.8, 18.7, 19.4, 19.8, 20.4, 21.4, 21.7, 23.1, 24.0, 24.4, 25.4, 27.8, 28.3, 30.0, and 32.8°.

A most preferred embodiment of the present invention is a polymorphic Form I of EP-13420 characterized by at least one strong XRD peak selected from 2-Theta angles 14.3, 14.5, 15.1, 18.8, 20.5, 23.2, 24.9, 25.6, 29.0, 34.1, 37.7, 38.1, 38.9, and 40.4°; a polymorphic Form II of EP-13420 characterized by at least one strong XRD peak selected from 2-Theta angles 11.2, 17.0, 19.9, 21.6, 25.5, 30.1, and 33.3°; or a polymorphic Form Ia characterized by at least one strong XRD peak selected from 2-Theta angles 9.7, 11.8, 13.2, 14.2, 14.9, 20.4, 21.7, 25.4, 27.8, 34.0, 40.6, and 44.7°.

The present invention also provides pharmaceutical compositions comprising substantially pure Form I, substantially pure Form II, substantially pure Form Ia, substantially pure monohydrate EP-13420 or substantially pure amorphous EP-13420, either as the sole active ingredient or in combination with other active ingredients including, but not limited to, other polymorphic forms of EP-13420 or other pharmaceutically active agents, at least one pharmaceutically acceptable carrier, diluent, and/or excipient. Combinations of more than one polymorphic form of EP-13420 are prepared via the described crystallization procedures or, for more precise combinations, via blending of pure or known polymorphic ratios. Preferred polymorphic combinations include, but are not limited to, Form I with Form II, Form Ia, monohydrate EP-13420 and/or amorphous EP-13420; Form II with Form I, Form Ia, monohydrate EP-13420 and/or amorphous EP-13420; monohydrate EP-13420 with Form I, Form II, and/or Form Ia EP-13420 and/or amorphous EP-13420; or amorphous EP-13420 with Form I, Form II, Form Ia EP-13420 and/or monohydrate EP13420.

Definitions

Listed below are definitions of various terms used to describe this invention. These definitions apply to the terms as they are used throughout this specification and claims, unless otherwise limited in specific instances, either individually or as part of a larger group.

As used herein, "substantially pure" means a compound having a purity of at least 90 percent, preferably at least 95 percent, and more preferably at least 98 percent.

The term "active ingredient(s)" or "active compound(s)," as used herein, refers to any of the polymorphic forms, or combinations thereof, delineated herein (i.e. Form I, Form II, Form Ia, amorphous EP-13420 or monohydrate EP-13420, or combinations thereof, or combinations with other polymorphic forms of EP-13420). Preferably, Form I or Form II EP-13420 in their pure forms are used in the pharmaceutical compositions and formulations of the present invention.

The term "subject" as used herein refers to an animal. Preferably the animal is a mammal. More preferably the mammal is a human. A subject also refers to, for example, dogs, cats, horses, cows, pigs, guinea pigs, fish, birds and the like.

By a "therapeutically effective amount" of an active ingredient or ingredients of the present invention is meant an amount of the active ingredient(s) which confer(s) a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the active ingredient(s) described herein may range from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific active ingredient employed; and like factors well known in the medical arts.

According to the methods of treatment of the present invention, bacterial infections, cystic fibrosis, and inflammatory conditions are treated or prevented in a subject such as a human or another animal by administering to the patient a therapeutically effective amount of an active ingredient or ingredients of the present invention, in such amounts and for such time as is necessary to achieve the desired result.

As used herein, unless otherwise indicated, the term "bacterial infection(s)" or "protozoa infections" includes, but is not limited to, bacterial infections and protozoa infections that occur in mammals, fish and birds as well as disorders related to bacterial infections and protozoa infections that may be treated or prevented by administering antibiotics such as polymorphic forms of the present invention. Such bacterial infections and protozoa infections and disorders related to such infections include, but are not limited to, the following: pneumonia, otitis media, sinusitus, bronchitis, tonsillitis, cystic fibrosis (CF) and mastoiditis, related to infection by *Streptococcus pneumoniae, Haemophilus influenzae, Moraxella catarrhalis, Staphylococcus aureus, Peptostreptococcus* spp., or *Pseudomonas* spp.; pharyngitis, rheumatic fever, and glomerulonephritis, related to infection by *Streptococcus pyogenes*, Groups C and G streptococci, *Clostridium diptheriae*, or *Actinobacillus haemolyticum;* respiratory tract infections related to infection by *Mycoplasma pneumoniae, Legionella pneumophila, Streptococcus pneumoniae, Haemophilus influenzae*, or *Chlamydia pneumoniae;* uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *S. pyogenes, S. agalactiae*, Streptococcal groups C-F (minute-colony streptococci), viridans streptococci, *Corynebacterium* spp., *Clostridium* spp., or *Bartonella henselae;* uncomplicated acute urinary tract infections related to infection by *S. saprophyticus* or *Enterococcus* spp.; urethritis and cervicitis; and sexually transmitted diseases related to infection by *Chlamydia trachomatis, Haemophilus ducreyi, Treponema pallidum, Ureaplasma urealyticum*, or *Nesseria gonorrheae;* toxin diseases related to infection by *S. aureus* (food poisoning and Toxic shock syndrome), or Groups A, S. and C streptococci; ulcers related to infection by *Helicobacter pylori;* systemic febrile syndromes related to infection by *Borrelia recurrentis;* Lyme disease related to infection by *Borrelia burgdorferi;* conjunctivitis, keratitis, and dacrocystitis related to infection by *C. trachomatis, N. gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare;* gastroenteritis related to infection by *Campylobacter jejuni;* intestinal protozoa related to infection by *Cryptosporidium* spp. odontogenic infection related to infection by viridans streptococci; persistent cough related to infection by *Bordetella pertussis;* gas gangrene related to infection by *Clostridium perfringens* or *Bacteroides* spp.; Skin infection by *S. aureus*, Propionibacterium acne; atherosclerosis related to infection by *Helicobacter pylori* or *Chlamydia pneumoniae;* or the like.

Bacterial infections and protozoa infections and disorders related to such infections that may be treated or prevented in animals include, but are not limited to, the following: bovine respiratory disease related to infection by *P. haemolytica., P. multocida, Mycoplasma bovis*, or *Bordetella* spp.; cow enteric disease related to infection by *E. coli* or protozoa (i.e., *coccidia, cryptosporidia*, etc.), dairy cow mastitis related to infection by *S. aureus, S. uberis, S. agalactiae, S. dysgalactiae, Klebsiella* spp., *Corynebacterium*, or *Enterococcus* spp.; swine respiratory disease related to infection by *A. pleuropneumoniae., P. multocida*, or *Mycoplasma* spp.;

swine enteric disease related to infection by *E. coli, Lawsonia intracellularis, Salmonella* spp., or *Serpulina hyodyisinteriae;* cow footrot related to infection by *Fusobacterium* spp.; cow metritis related to infection by *E. coli;* cow hairy warts related to Infection by *Fusobacterium necrophorum* or *Bacteroides nodosus;* cow pink-eye related to infection by *Moraxella bovis,* cow premature abortion related to infection by *protozoa* (i.e. *neosporium*); urinary tract infection in dogs and cats related to infection by *E. coli;* skin and soft tissue infections in dogs and cats related to infection by *S. epidermidis, S. intermedius,* coagulase neg. *Staphylococcus* or *P. multocida;* and dental or mouth infections in dogs and oats related to infection by *Alcaligenes* spp., *Bacteroides* spp., *Clostridium* spp., *Enterobacter* spp., *Eubacterium* spp., *Peptostreptococcus* spp., *Porphfyromonas* spp., *Campylobacter* spp., *Actinomyces* spp., *Erysipelothrix* spp., *Rhodococcus* spp., *Trypanosoma* spp., *Plasmodium* spp., *Babesia* spp., *Toxoplasma* spp., *Pneumocystis* spp., *Leishmania* spp., and *Trichomonas* spp. or *Prevotella* spp. Other bacterial infections and protozoa infections and disorders related to such infections that may be treated or prevented in accord with the method of the present invention are referred to in J. P. Sanford at al., "The Sanford Guide To Antimicrobial Therapy," 26th Edition, (Antimicrobial Therapy, Inc., 1996).

The invention further provides compositions and methods of treating patients suffering from an inflammatory condition comprising administering to a patient in need thereof, a therapeutically effective amount of at least one compound of the invention. Specific examples of inflammatory conditions treatable according to the invention include, but are not limited to, scleritis; epi-scleritis; allergic conjunctivitis; pulmonary inflammatory diseases, particularly cystic fibrosis (CF), asthma, chronic obstructive pulmonary disease (COPD), allergic bronchopulmonary aspergillosis (ABPA), and sarcoidosis; procto-sigmoiditis; allergic rhinitis; arthritis; tendonitis; apthous stomatitis; and inflammatory bowel disease.

The invention further provides compositions and methods for i) prophylactic treatment of those patients susceptible to the symptoms CF including pulmonary infection and inflammation associated with CF, ii) treatment at the initial onset of symptoms of pulmonary infection and inflammation associated with CF, and iii) treatment of ongoing or relapsing symptoms of infection and inflammation associated with CF. In accordance with the invention a compound of the invention is administered to a patient in need of treatment for CF, in amount sufficient to prevent, diminish or eradicate symptoms of CF including chronic pulmonary inflammation and infection.

Pharmaceutical Compositions

Pharmaceutical compositions of the present invention comprise a therapeutically effective amount of any one of the active ingredients of the present invention, or a combination thereof, optionally formulated together with one or more pharmaceutically acceptable carriers or excipients.

As used herein, the term "pharmaceutically acceptable carrier or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

In one embodiment a preferred suspension formulation of the invention comprises 60-1600 mg of amorphous EP-13420 in a simple syrup:sterile water (4:56, v:v) solution.

In another embodiment, suspensions are made that advantageously have the taste of the pharmaceutical ingredients masked such as that described in U.S. Pat. Pub. No: 2004/0142029 incorporated herein by reference. One preferred pharmaceutical formulation of EP 13420 (Form I, Form Ia, Form II, monohydrate, amorphous, or any combination thereof) having a masked taste, preferably in the form of a suspension in an aqueous vehicle, comprises: a) a cellulosic polymer which is soluble in organic solvents but substantially insoluble in water, regardless of the pH; a methacrylic polymer which is soluble in an acid medium and substantially insoluble at a neutral or alkaline pH and an active ingredient distributed in a homogeneous manner and in the molecular state in the mixture, which is in the form of an atomized matrix; b) a pharmaceutically acceptable alkaline agent of an organic nature or an alkaline salt; and c) an adsorbent agent. The cellulosic polymer and the methacrylic polymer are preferably respectively, ethylcellulose and a cationic polymer formed from 2-dimethylaminoethyl methacrylate and neutral methacrylates. The alkaline agent and the adsorbent agent are preferably meglumine, lysine, sodium and potassium citrate and sodium and potassium carbonate, magnesium aluminum silicate and talc. The cellulosic polymer is present in the atomized matrix in a proportion ranging from about 30% to about 50% by weight and the methacrylic polymer is present in a proportion ranging from about 10% to about 25% by weight; and EP 13420 is present in the atomized matrix at a maximum level of about 50% by weight. In one embodiment, preferred proportions of cellulosic and methacrylic polymers in the matrix range respectively from about 40% to about 45% and from about 15% to about 20% by weight, and in that the maximum amount of EP 13420 in the matrix is about 30% by weight. The formulation may optionally include within the matrix a hydrophobic plasticizing agent and/or an antioxidant agent. The formulation may also optionally one or more elements chosen from preservative agents, sweetening agents, thickening agents and flavoring agents.

In another taste masking embodiment, the formulation comprises from about 15 to about 30% of EP 13420 in any form or any combination of forms mixed with from about 60% to about 80% of an ester of glycerol or of a fatty acid, to which a wax is optionally added, and to which a surfactant is added, and wherein the composition is prepared by a spray-cooling process which can produce a particle size of less than about 350 microns. The esters of glycerol or of fatty acid used in this embodiment have the following characteristics: melting temperature in the range of from about 25.degree. C. to about 100.degree. C., preferably from about 25.degree. C. to about 70.degree. C. and stability in the molten state. The ester of glycerol may be chosen from glyceryl stearate or glyceryl palmitostearate, in particular Precirol®. The ester of glycerol is advantageously between 50 and 85% by weight of the total mixture of the composition; it is preferably between 60 and 80% by weight, and more particularly between 70 and 80% by weight. The wax which can be optionally added may advantageously be carnauba wax, or it may also be chosen from paraffin or beeswax or candelilla wax. When a wax is added to the composition, it may be added in a proportion of from about 4% to about 10% by weight of the total mixture of the composition and in a ratio of from about 5% to about 20% with respect to the ester of glycerol introduced. When a fatty acid is introduced into the composition, this fatty acid is advantageously chosen from palmitic, myristic or stearic acid. The fatty acid is introduced in a proportion of from about 60% to about 80% by weight of the total mixture of the composition. The surfactant introduced into the composition is advantageously chosen from lecithins, in particular soybean lecithin, or surfactants of the family of sorbitan esters having an HLB of less than 7. The surfactant is added in a proportion of from about 1% to about 3% by weight of the total mixture of the composition.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microcapsule matrices of the drug in biodegradable polymers such as polylactide-coglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, crospovidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

The invention provides two preferred capsule formulations or "blends". The formulation of the two preferred blends each comprise:

| Blend | Weight Composition for 100 mg Strength capsule |
|---|---|
| #1) EP-013420 amorphous | 25.0 |
| Anhydrous Lactose | 72.25 |

-continued

| Blend | Weight Composition for 100 mg Strength capsule |
| --- | --- |
| Crospovidone | 2.0 |
| Magnesium Stearate | 0.75 |
| Full Weight | 400 |
| #2) EP-013420 amorphous | 30.8 |
| Microsrystalline Cellulose | 66.45 |
| Sodium Starch Glycolate | 2.0 |
| Magnesium Stearate | 0.75 |
| Full Weight | 325 |

In another embodiment, soft bite capsules comprising Blends # 1 and #2 described above is provided. Soft bite gelatin capsules are well known in the art.

In another embodiment, a soft-bite gelatin capsule for transmucosal administration is provided comprising about 0.01-85% by weight of at least one form of an active ingredient of the invention, non-polar solvent about 4-99.99%, emulsifier about 0-20%, and preferably wherein any fill composition contains less than about 10% of water, and optionally also comprising, by weight of the composition, a flavoring agent about 0.01-10% (all percentages in weight % of total composition). Preferably, the soft bite gelatin capsule comprises, non-polar solvent about 21.5-99.975% by weight, emulsifier about 0-15% by weight, active ingredient about 0.025-70% by weight, flavoring agent about 1-8% by weight, and even more preferably, nonpolar solvent about 28.5-97.9% by weight, emulsifier about 0-10% by weight, active ingredient about 0.1-65.0% by weight, flavoring agent about 2-6%. In another embodiment, a soft-bite gelatin capsule for transmucosal administration is provided comprising about 0.01-65% of active ingredient, polar solvent about 25-99.89%, emulsifier about 0-20%, active ingredient, and preferably such composition contains less than about 10% by weight of water, and optionally also comprises flavoring agent about 01-10% by weight. Preferably, the soft bite gelatin capsule comprises, polar solvent about 37-99.95%, emulsifier about 0-15%, active ingredient about 0.025-55%, flavoring agent about about 1-8%, and more preferably, polar solvent about 44-96.925%, emulsifier about 0-10%, active ingredient about 0.075-50%, flavoring agent about 2-6% (all percentages in weight % of total composition).

In another embodiment, the invention provides a tablet comprising an alginate matrix consisting of a water soluble alginate salt and a complex salt of alginic acid, active ingredient that is any form of EP 13420 described herein or any combination thereof, an inorganic salt capable of donating a proton and having a pKa value in water of 4.0 to 9.0. Alginate formulations are generally described in WO 2004/056344 incorporated herein by reference. An alginate matrix suitable with the invention comprises a water-soluble alginate and a complex salt of alginic acid. The water soluble alginate in the composition is typically an alkali salt of alginic acid such as a potassium or sodium salt, or a magnesium salt or an ammonium salt. A complex salt of alginic acid is typically a sodium-calcium complex salt of alginic acid. The weigh ratio of a soluble alginate to a complex salt of alginic acid may vary from about 16:1 to 1:1 preferably from about 8:1 to 2:1. The same ratio applies to the ratio of sodium alginate to sodium calcium alginate. Preferably the amount of soluble alginate in a composition varies from about 6% to about 25% of the total weight of the composition and the amount of the complex salt of alginic acid varies from about 0.5% to about 10% of the total weight of the composition. The mixture may be granulated according to conventional granulation technology and by drying the obtained granules using conventional drying technology. The dried granules may optionally be resized. In the case the composition is a capsule, the granules are filed into the capsule, (e.g. gelatin capsule). In the case the composition is a tablet, the granules may be mixed with glindants/lubricants and compressed into tablets using conventional technology.

In another embodiment, the invention provides a "fast melt" formulation. Such fast melt formulations are typically in the form of a tablet or lozenge that dissolve or disperse in a patient's mouth within a minute without the need of water or chewing. Such fast melt formulations are described in WO 03/074029, incorporated herein by reference. In certain embodiments, the formulation comprises a non-compressed, free flowing plurality of particles comprising at least one form of EP 13420 of the invention (Form I, Form Ia, Form II, monohydrate, amorphous or any combination thereof) and a water-soluble excipient, the particles having a mean diameter of greater than 10 microns to about 1 mm, the particles comprising at least about 50% active ingredient and the formulation dissolving in the patients mouth within 1 minute after administration without the co-administration of fluid. The water soluble excipient of the formulation can be a sugar alcohol including, but not limited to sorbitol, manitol, maltitol,reduced starch saccharide, xylitol, reduced parationse, erythritol and combinations thereof. Other suitable water soluble excipients include gelatin, partially hydrolyzed gelatin, hydrolyzed dextran, dextrin, alginate and mixtures thereof. Salivary stimulants such as citric acid, carbonate sources and the like and sweeners such as saccharin salts, and aspartame may optionally be included.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons. In one embodiment, the invention provides a formulation comprising at least one form of EP-13420 (Form I, Form Ia, Form II, monohydrate, amorphous or any combination thereof) in a buccal aersol spray comprising polar or non-polar solvents similar to that described in U.S. Pat Pub 2003/0082107, incorporated herein by reference. In this embodiment a propellant-free buccal spray formulation for transmucosal administration comprises at least one form of EP-13420 (Form I, Form Ia, Form II, monohydrate, amorphous or any combination thereof) and a polar or non-polar solvent in an amount between about 30-99%. Optionally a propellant may be used in the amount of about 2-10% by weight of the total composition if a propellant buccal spray is desired.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The total daily dose of the pharmaceutical compositions of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The pharmaceutical compositions, as described herein, can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of a therapeutically effective amount of a pharmaceutical composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active ingredient (w/w). Alternatively, such preparations may contain from about 20% to about 80% active ingredient.

Lower or higher doses than those recited above may be required. Specific dosage and treatment regimens for any particular patient will depend upon a variety of factors, including the activity of the specific pharmaceutical composition employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of any one the active ingredients, or a combination thereof, of the present invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

When the pharmaceutical compositions of this invention comprise a combination of an active ingredient of the present invention and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with active ingredients of this invention in a single composition.

In one preferred embodiment therapeutic compositions of the invention are administered by pulmonary delivery. For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. In general, particles ranging from about 1 to 10 microns in size are within the respirable range. The therapeutic compositions containing at least one form of EP-13420 (Form I, Form Ia, Form II, monohydrate, amorphous or any combination thereof), are preferably administered by direct inhalation into the respiratory system for delivery as a mist or other aerosol or dry powder. Particles of non-respirable size which are included in the aerosol tend to be deposited in the throat and swallowed; thus the quantity of non-respirable particles in the aerosol is preferably minimized. Delivery of aerosolized therapeutics, particularly aerosolized antibiotics, is known in the art (see, for example U.S. Pat. No. 5,767,068 to VanDevanter et al., U.S. Pat. No. 5,508,269 to Smith et al., and WO 98/43,650 by Montgomery, all of which are incorporated herein by reference). A discussion of pulmonary delivery of antibiotics is also found in U.S. Pat. No. 6,014,969, incorporated herein by reference.

The dosage of active compound via the pulmonary route of delivery will vary depending on the condition being treated and the state of the subject, but generally may be an amount sufficient to achieve dissolved concentrations of active compound on the airway surfaces of the subject. Depending upon the solubility of the particular formulation of active compound administered, the daily dose may be divided among one or several unit dose administrations. The daily dose by weight will depend upon the age and condition of the subject. Such a daily dose of active compound ranges from about 0.20 mg/kg per day to about as 2.0 mg per day, and more preferably from about 0.1 to about 1 mg/kg and most preferably from about 0.200 mg/kg to about 0.650 mg/kg. The doses of the active compound may be provided as one or several prepackaged units.

The pharmaceutical compositions of this invention can be administered orally to fish by blending said pharmaceutical compositions into fish feed or said pharmaceutical compositions may be dissolved in water in which infected fish are placed, a method commonly referred to as a medicated bath. The dosage for the treatment of fish differs depending upon the purpose of administration (prevention or cure of disease) and type of administration, size and extent of infection of the fish to be treated. Generally, a dosage of 5-1000 mg, preferably 20-100 mg, per kg of body weight of fish may be administered per day, either at one time or divided into several times. It will be recognized that the above-specified dosage is only a general range which may be reduced or increased depending upon the age, body weight, condition of disease, etc. of the fish.

Unless otherwise defined, all technical and scientific terms used herein are accorded the meaning commonly known to one of ordinary skill in the art. All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of Form I EP-13420

Crude EP-13420 (0.65 kg) in ethyl acetate was concentrated in vacuo until approximately 1.5 L remains. The residue was then diluted with ethanol (5.0 L) and concentrated until approximately 3.5 L remain. To this residue was added purified water while maintaining a vacuum and a temperature of approximately 80° C. The vacuum was released and the aqueous solution was further agitated at 75° C. while allowing solution to cool to a temperature of approximately 20° C. over a period of 3 hrs. Once the solution had reached a temperature of 20° C., the aqueous slurry was agitated for an additional period of 2 hrs and subsequently filtered. The filtered material was washed with chilled (less than 5° C.) (1:2) ethanol/water (0.3 L) while retaining the mother liquor and washing solution for future use. After drying the crystalline material, it was dissolved once again in ethanol and recrystallized in the same manner as previously described to arrive upon Form I of EP-13420.

Example 2

Preparation of Form II EP-13420

EP-13420 (100 mg) was dissolved in ethanol (0.35 mL) and the resulting solution was added to distilled water (2 mL) slowly while stirring to form a slurry. The slurry was then stirred at room temperature for 2 hours. The white crystalline solid was filtered and dried to yield Form II of EP-13420.

Example 3

Preparation of Form Ia EP-13420

To a solution of EP-13420 (100 mg) in ethyl acetate (0.24 mL) was added n-heptane (2 mL) slowly while stirring to form a slurry. The slurry was then stirred at room temperature for 2 hours. The resulting crystalline material was then filtered and dried to yield Form Ia of EP-13420.

Example 4

Preparation of Amorphous form EP-13420

EP-13420 (100 mg) was dissolved in ethyl acetate (1 mL) and the resulting solution was concentrated by stirring at 50° C. The resulting solid was dried in vacuo to yield amorphous form EP-13420.

In a second experiment, EP-013420, (67.5 g, 80 mmol) was dissolved in ethanol (250 ml, 3.7 volume) at 40° C. Removal of solvent by rotavap (bath temperature: 40° C.) and then drying at 30° C. for 48 hours afforded EP-013420 as a white amorphous solid (m.p. <140° C.).

A wide variety of other organic solvents are suitable for amorphous form formation, e.g. alcoholic solvents such as methanol, isopropyl alcohol, butanol, etc; organic esters such as ethyl acetate, isopropyl ethyl acetate etc; organic ethers such as butyl methyl ether, diethyl ether, etc; and other common organic solvents such as acetonitrile, MEK, THF, DMF.

In a third experiment, amorphous EP 13420 is prepared on an industrial scale by dissolving EP-13420 in any of the above-mentioned organic solvents suitable for amorphous form formation and the solvent is removed by spray drying. Suitable spray drying techniques are well known in the art and may be found in K Masters, *Spray Drying Handbook* ($5^{th}$ edition), John Wiley and Sons, Inc., New York, N.Y. (1991).

Example 5

Preparation of EP-13420 Monohydrate by Evaporation

Figure 9:
FIG. 9 is an SEM image of EP-13420 Form I.
Figure 10A:
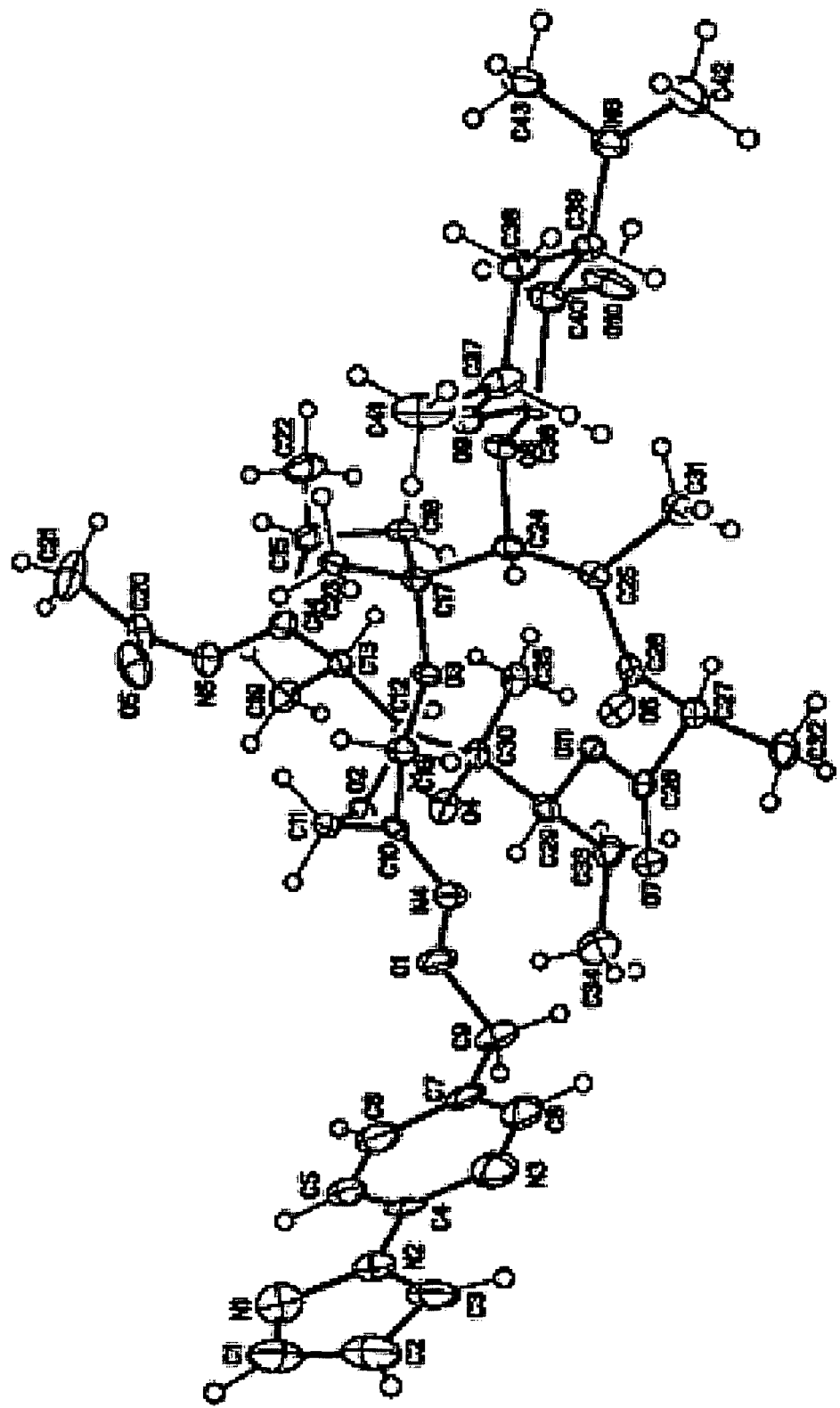
FIGS. 10A and 10B is an illustration of crystal structures of EP-13420 Form I and monohydrate, respectively.
Figure 10B:
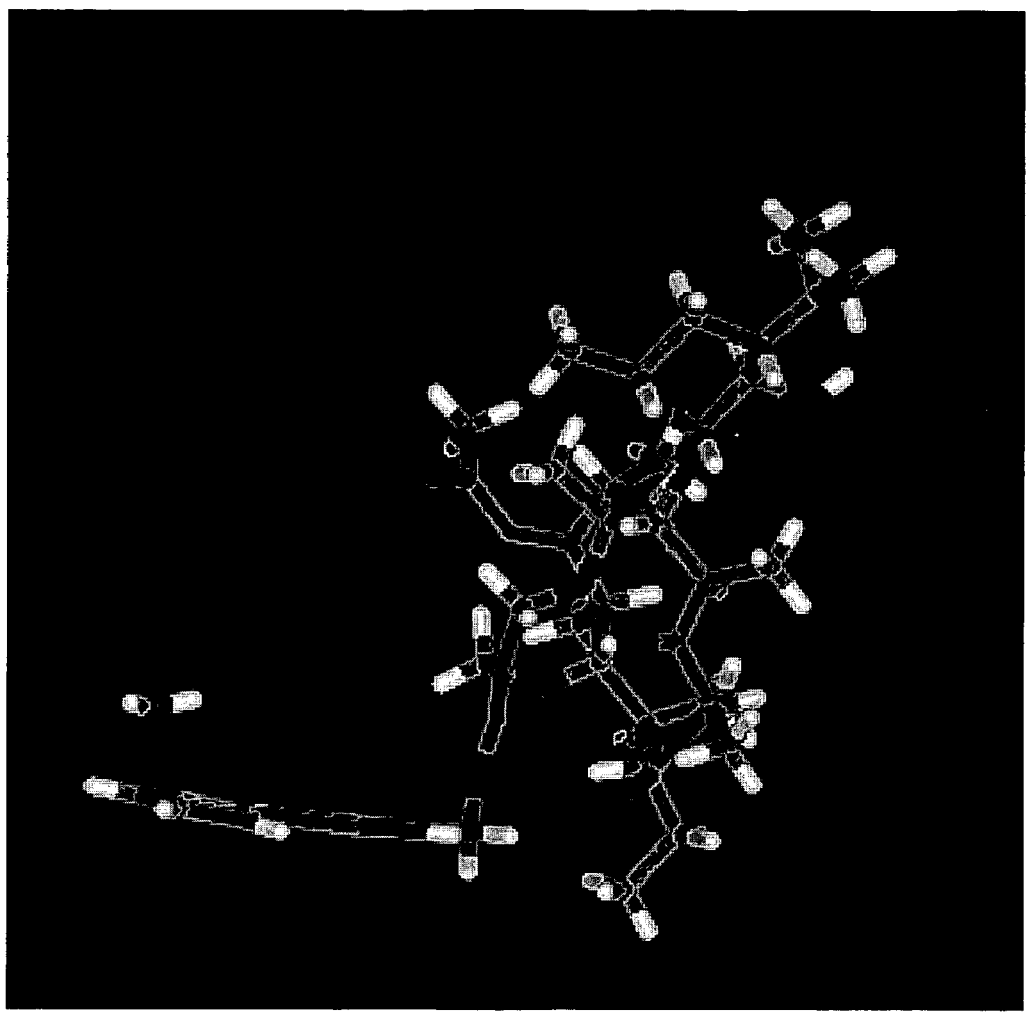
Figure 11A:
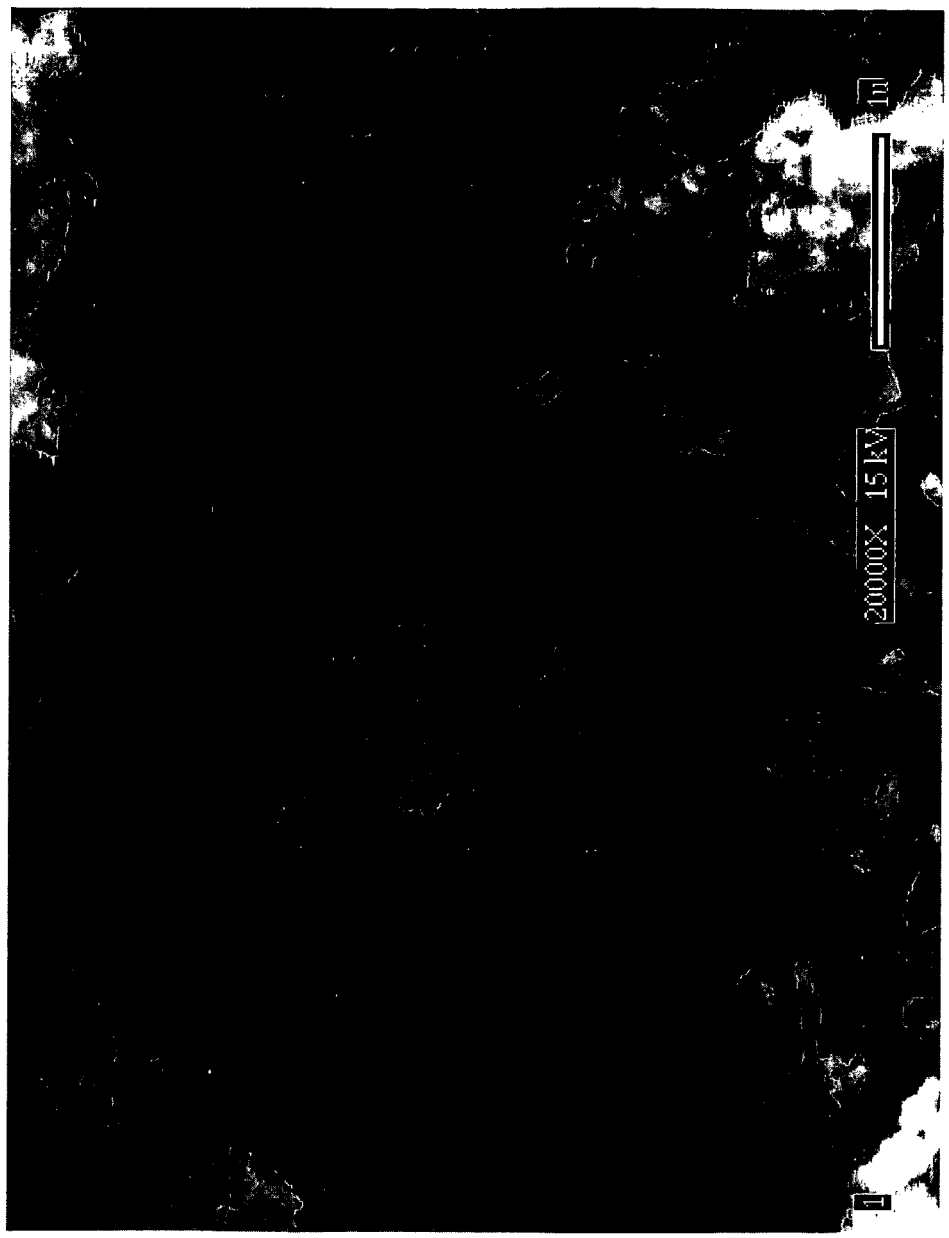
Figure 11B:
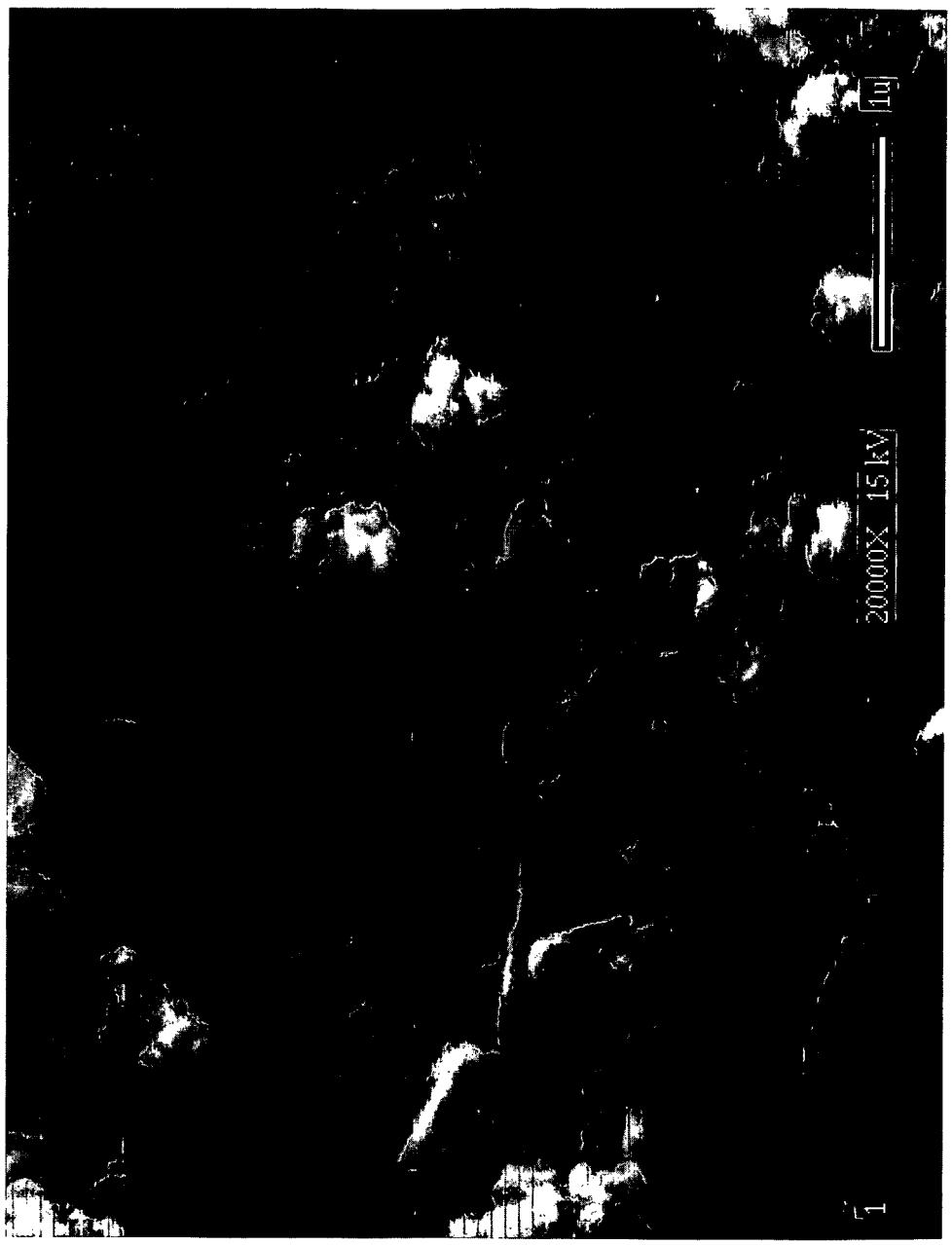
Figure 11C:
Figure 12:

EP-13420 (31 mg, purity>98%, HPLC area) was charged into a one-dram vial and dissolved in acetone (1.6 ml). Purified water (0.8 ml) was added. The mixture was warmed, as necessary, to obtain a clear colorless solution. Slow evaporation over 2 weeks afforded single crystals of EP-13420 monohydrate. The crystals so obtained appear to be needles, as shown in FIG. 9.

Example 6

Preparation of Form I by Antisolvent Addition

Saturated solutions of drug substance were prepared by adding drug substance to a solvent at room temperature and then heating until all solids were dissolved. An antisolvent was added to induce precipitation of a higher energy form. Representative solvents, antisolvents and crystalline solvents were chosen. The following solvents/antisolvents resulted in Form I formation: MEK/heptane; MeOH/water; EtOac/heptane; THF/heptane; IPAc/Heptane; EtOH/water; MIBK/heptane. The following solvents/antisolvents resulted in Form Ia formation: MEK/heptane; EtOac/heptane; THF/ heptane; IPAc/Heptane; and MIBK/heptane. EtOH/water also resulted in Form II formation.

Example 7

Saturated or near saturated solutions were prepared in a solvent and added to a larger volume of miscible antisolvent at the same or lower temperature. The following solvents/antisolvents resulted in Form II formation: MEK/heptane; MeOH/water; THF/heptane; and EtOH/water. The following solvents/antisolvents resulted in Form I or Ia formation: /heptane; IPAc/Heptane; and MIBK/heptane.

Example 8

Antibacterial Activity

Susceptibility tests can be used to quantitatively measure the in vitro activity of an antimicrobial agent against a given bacterial isolate. Compounds are tested for in vitro antibacterial activity by a micro-dilution method. Minimal Inhibitory Concentration (MIC) is determined in 96 well microtiter plates utilizing the appropriate Mueller Hinton Broth medium (CAMHB) for the observed bacterial isolates. Antimicrobial agents are serially diluted (2-fold) in DMSO to produce a concentration range from about 64 µg/ml to about 0.03 µg/ml. The diluted compounds (2 µl/well) are then transferred into sterile, uninoculated CAMHB (0.2 mL) by use of a 96 fixed tip-pipetting station. The inoculum for each bacterial strain is standardized to $5 \times 10^5$ CFU/mL by optical comparison to a 0.5 McFarland turbidity standard. The plates are inoculated with 10 µl/well of adjusted bacterial inoculum. The 96 well plates are covered and incubated at 35 +/−2° C. for 24 hours in ambient air environment. Following incubation, plate wells are visually examined by Optical Density measurement for the presence of growth (turbidity). The lowest concentration of an antimicrobial agent at which no visible growth occurs is defined as the MIC. The active ingredients of the invention typically will demonstrate MICs in the range from about 64 µg/ml to about 0.03 µg/ml.

All in vitro testing follows the guidelines described in the Approved Standards M7-A4 protocol, published by the National Committee for Clinical Laboratory Standards (NCCLS).

Although the invention has been described with respect to various preferred embodiments, it is not intended to be limited thereto, but rather those skilled in the art will recognize that variations and modifications may be made therein which are within the spirit of the invention and the scope of the appended claims.

What is claimed:

1. A polymorphic form of EP-13420, designated Form I EP-13420, having an X-ray diffraction pattern with at least one strong peak located at a 2-Theta (2θ) angle selected from: 14.3, 14.5, 15.1, 18.8, 20.5, 23.2, 24.9, 25.6, 29.0, 34.1, 37.7, 38.1, 38.9, and 40.4°.

2. The polymorphic Form I of claim 1 having a differential scanning calorimetry endotherm at 173° C. (onset at 167° C.).

3. The polymorphic Form I of claim 1 in substantially pure form.

4. A polymorphic form of EP-13420 characterized by the XRD pattern of FIG. 1.

5. A pharmaceutical composition comprising a therapeutically effective amount of Form I EP 13420, in combination with a pharmaceutically acceptable carrier.

6. The pharmaceutical composition according to claim 5 for oral administration.

7. The pharmaceutical composition according to claim 6 in capsule form.

8. The pharmaceutical composition according to claim 6 in tablet form.

9. The pharmaceutical composition according to claim 5 wherein at least one pharmaceutically acceptable carrier is selected from the group consisting of fillers, extenders, binders, humectants, disintegrating agents, solution retarding agents, absorption accelerators, wetting agents, absorbents, lubricants, buffering agents, coatings, and opacifying agents.

10. A method of treating a bacterial infection in a subject in need of such treatment comprising the step of administering to the patient the pharmaceutical composition of claim 5.

* * * * *